(12) United States Patent
Cunniffe et al.

(10) Patent No.: US 7,727,268 B2
(45) Date of Patent: Jun. 1, 2010

(54) METHODS AND DEVICES FOR PLACING A FISTULA DEVICE IN FLUID COMMUNICATION WITH A TARGET VESSEL

(75) Inventors: Brendan Cunniffe, Galway (IE); Niall Duffy, Galway (IE); Noel Coyle, Galway (IE); Richard William Alan Francis, Minneapolis, MN (US); Ronan Thornton, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 1728 days.

(21) Appl. No.: 10/887,541

(22) Filed: Jul. 7, 2004

(65) Prior Publication Data

US 2005/0033401 A1 Feb. 10, 2005

(30) Foreign Application Priority Data

Jul. 17, 2003 (IE) .................................. S2003/0531

(51) Int. Cl.
*A61F 2/06* (2006.01)
(52) U.S. Cl. ..................................... 623/1.11; 606/194
(58) Field of Classification Search ................. 606/194, 606/159, 153, 151, 213; 623/1.11, 1.22, 623/1.14, 1.13
See application file for complete search history.

(56) References Cited

U.S. PATENT DOCUMENTS

| | | | |
|---|---|---|---|
| 5,287,861 A | 2/1994 | Wilk | |
| 5,409,019 A | 4/1995 | Wilk | |
| 5,575,685 A | 11/1996 | Ittah et al. | |
| 5,755,682 A | 5/1998 | Knudson et al. | |
| 5,824,071 A | 10/1998 | Nelson et al. | |
| 5,830,222 A | 11/1998 | Makower | |
| 5,908,029 A | 6/1999 | Knudson et al. | |
| 5,944,019 A | 8/1999 | Knudson et al. | |
| 5,984,956 A | 11/1999 | Tweden et al. | |
| 6,026,814 A | 2/2000 | LaFontaine et al. | |
| 6,029,672 A | 2/2000 | Vanney et al. | |
| 6,035,856 A | 3/2000 | LaFontaine et al. | |
| 6,053,942 A | 4/2000 | Eno et al. | |
| 6,068,638 A | 5/2000 | Makower | |
| 6,076,529 A | 6/2000 | Vanney et al. | |
| 6,092,526 A | 7/2000 | LaFontaine et al. | |
| 6,093,166 A | 7/2000 | Knudson et al. | |
| 6,099,542 A | 8/2000 | Cohn et al. | |
| 6,102,941 A | 8/2000 | Tweden et al. | |
| 6,113,630 A | 9/2000 | Vanney et al. | |
| 6,113,823 A | 9/2000 | Eno | |
| 6,123,682 A | 9/2000 | Knudson et al. | |
| 6,182,668 B1 | 2/2001 | Tweden et al. | |
| 6,193,726 B1 | 2/2001 | Vanney | |

(Continued)

FOREIGN PATENT DOCUMENTS

EP 0876803 4/1998

(Continued)

*Primary Examiner*—Anhtuan T Nguyen
*Assistant Examiner*—Julie A Szpira

(57) ABSTRACT

According to an aspect of the invention there is provided an apparatus for deploying a fistula device. The apparatus comprises an elongate cover member having a proximal end and a distal end, and an elongate support member within the cover member for supporting the fistula device and configured for relative movement with respect to the cover member so as to release the fistula device at a desired location.

10 Claims, 7 Drawing Sheets

U.S. PATENT DOCUMENTS

| | | |
|---|---|---|
| 6,196,230 B1 | 3/2001 | Hall et al. |
| 6,197,050 B1 | 3/2001 | Eno et al. |
| 6,214,041 B1 | 4/2001 | Tweden et al. |
| 6,221,081 B1 * | 4/2001 | Mikus et al. ................. 606/108 |
| 6,223,752 B1 | 5/2001 | Vanney et al. |
| 6,231,597 B1 * | 5/2001 | Deem et al. ................. 623/1.12 |
| 6,237,607 B1 | 5/2001 | Vanney et al. |
| 6,302,875 B1 * | 10/2001 | Makower et al. ............. 604/528 |
| 6,375,615 B1 * | 4/2002 | Flaherty et al. ............. 600/439 |
| 2002/0004663 A1 * | 1/2002 | Gittings et al. .............. 606/153 |
| 2003/0097095 A1 * | 5/2003 | Brady et al. ............ 604/164.13 |
| 2003/0109886 A1 | 6/2003 | Keegan et al. |
| 2004/0133225 A1 * | 7/2004 | Makower .................... 606/167 |

FOREIGN PATENT DOCUMENTS

| | | |
|---|---|---|
| WO | 9808456 | 3/1998 |
| WO | 9940868 | 2/1999 |
| WO | 0041632 | 1/2000 |
| WO | 0041633 | 1/2000 |
| WO | WO00/06607 | 2/2000 |
| WO | WO00/06609 | 2/2000 |
| WO | 0015147 | 3/2000 |
| WO | 0015148 | 3/2000 |
| WO | 0015149 | 3/2000 |
| WO | 0021436 | 4/2000 |
| WO | 0021461 | 4/2000 |
| WO | 0021463 | 4/2000 |
| WO | WO00/21461 | 4/2000 |
| WO | 0066007 | 5/2000 |
| WO | 0066009 | 5/2000 |
| WO | WO00/78246 | 12/2000 |
| WO | 0110341 | 2/2001 |
| WO | 0110347 | 2/2001 |
| WO | 0110348 | 2/2001 |
| WO | 0110349 | 2/2001 |
| WO | 0117440 | 3/2001 |
| WO | 0117456 | 3/2001 |

* cited by examiner

METHODS AND DEVICES FOR PLACING A FISTULA DEVICE IN FLUID COMMUNICATION WITH A TARGET VESSEL

FIELD OF THE INVENTION

The present invention concerns relates to methods and devices for placing a fistula device in fluid communication with a target vessel. The methods and devices of the invention are particularly for use in the treatment of heart disease. The term "fistula device" as used herein is to be understood to include a conduit, shunt or stent and the like.

BACKGROUND OF THE INVENTION

Heart disease as referred to herein is caused by the formation of atherosclerotic lesions within coronary arteries. Atherosclerosis involves changes to the intima arterial vessel wall. Atherosclerosis is characterized by a progressive accumulation of plaque about the arterial wall and associated loss of elasticity. Artery walls consist of three layers: a layer of connective tissue, a second layer of smooth muscle cells and elastic connective tissue, and a third layer of endothelial cells. The endothelial cells are flattened and elongated and they overlap and are aligned in the direction of the blood flow. They have cell membrane surfaces which provide them with an "anti-stick" characteristic so as to avoid the build-up of substances on the inner surface of the blood vessel lumen.

Mechanical or chemical injury of the endothelial cells or damage to their non-stick surface provides sites for thrombocyte adhesion and leads to the formation of thrombi in the arterial wall. Some chemicals e.g. homocysteine and nicotine permanently open up the junctions between the endothelial cells perforating the endothelial layer. This damage allows monocytes (white blood cells) to stick to the formerly non-stick surface and pass into the intima itself, where they become active macrophages and scavenge oxidised LDL cholesterol. Aggregations of lipid-rich macrophages (known as foam cells) constitute early lesions which are often referred to as fatty streaks.

So called fatty streaks interfere with normal laminar blood flow, particularly at the site of blood vessel branches and bifurcations. They also continue to aggravate the surrounding tissue and provide sites for further thrombocyte adhesion. Over time, fatty streaks grow and connective tissue forms thereby progressively narrowing the lumen and consequently progressively restricting blood flow distally of the occlusion. Atherosclerosis may lead to myocardial infarction and angina pectoris and also contributes to the occurrences of strokes.

Currently, approximately 16 million U.S. citizens have diabetes and approximately 50% are unaware of their condition. Worldwide, approximately 110 million people suffer diabetes and recent projections suggest that this figure will have doubled in 10 years. The risk of heart disease and stroke is three to fives times greater for males with diabetes. Female diabetics are normally protected from heart disease until the menopause, however by the age of 55 they are seven times more likely to have heart disease than women without diabetes. Sixty five percent of people with diabetes also have high blood pressure and heart disease is the most common cause of death in patients with diabetes.

As a consequence of having diabetes, the blood vessel walls of a typical sufferer become thinned. If a balloon angioplasty procedure is indicated, this thinning of the walls presents two serious consequences. Firstly, since the vessel walls are thinner, they are mechanically weaker than healthy vessels and consequently they are more likely to rupture and sustain trauma. The second consequence of diabetes is that sufferers are more likely to suffer follow on post balloon angioplasty complications.

Studies by the US National Heart, Lung & Blood Institute comparing the effects of both balloon angioplasty and bypass procedures between groups of diabetic and non-diabetic and those patients with non-medication dependant diabetes indicates virtually identical long term outcomes, viz., a five year mortality rate of approximately 9%. Similar studies on medication dependant patients, i.e. those injecting insulin, indicated a five year mortality rate of 19% for post bypass surgery and 35% for post balloon angioplasty. Another interesting observation was that medication dependant diabetics are less likely to experience angina, the chest pain associated with oxygen deprivation through reduced blood flow.

On the basis of the preceding information it is evident that medication dependant diabetic patients fare considerably better when treated by bypass surgery than balloon angioplasty. Although there have been recent successes through employment of endoscopic coronary artery bypass graft (ECABG) techniques, bypass surgery typically involves sternotomy, and consequently considerable trauma, pain, and associated relatively long bed residence. Furthermore, although beating heart operations are becoming more common due to the employment of devices such as the Medtronic Endo Octopus™ stabilizer, many coronary artery bypass graft (CABG) techniques require the heart to be arrested. Amongst the possible complications encountered with CABG are the following:

Sternitis and mediastinitis, Haemolysis, Heparin rebound phenomena, Complement activation, Deterioration of the immune system, Poor appetite, Insomnia, Depression, Visual deficit, Memory deficit, Intellectual deficit, and Loss of sexual ability.

Thus, there is a need for a method by which the advantages of minimally invasive procedures and the long-term relative success rate of CABG can be combined. Such a method would be particularly suitable as a treatment for medication dependant diabetics.

The function of the methods and devices of the invention is to re-establish and maintain an adequate supply of oxygenated blood to heart tissue in areas formerly starved of oxygen. These regions of oxygen starved tissue are typically distal of an atherosclerotic lesion. The devices and methods described herein source oxygenated blood from a chamber of the heart, for example from the left ventricle (LV) and redirect this blood via a connecting conduit (shunt) to a portion of the left anterior descending coronary artery (LAD) or circumflex artery lying distal of the lesion.

U.S. Pat. No. 6,123,682 discloses a closed chest coronary bypass implant (conduit) for forming a channel directly from the left ventricle of the heart into a coronary artery distal to an obstruction or narrowing. In various embodiments disclosed, the implant can be used in an open-chest procedure, closed-chest procedure or alternatively, by catheter access to the coronary arterial vasculature and chambers of the heart via two incision sites, one in the groin and one in the right superior-anterior chest. The implant disclosed can be an L-shaped or T-shaped hollow stent which may be rigid or may have varying flexibilities. The device disclosed includes a capacitance pressure reservoir for storing pressurized blood during systole, for delivery to the heart muscles during diastole when pressures are reduced. In the catheter-controlled embodiment, a channel is ablated through both the chambers of the heart and the coronary artery wall using an ablating tip.

International Patent Specification No. WO 00/21461 discloses methods and devices for delivering a conduit into a heart wall to place a coronary vessel in communication with a heart chamber and for removing tissue from the vessel or heart wall to facilitate such communication.

WO 00/6607 discloses methods and devices for placing a conduit in fluid communication with a target vessel. The device includes a handle, a shaft assembly and a conduit having a vessel coupling.

WO 00/6609 also discloses methods and devices for forming a fistula device to place a target vessel in fluid communication with a source of blood, such as the aorta or a heart chamber.

BRIEF SUMMARY OF THE INVENTION

The present invention seeks to alleviate the disadvantages of the known devices by providing an improved method and device for placing a conduit in fluid communication with a target vessel.

Accordingly, the present invention provides a delivery apparatus for delivering a fistula device into a wall of a patient's heart to place the fistula device in communication with a heart chamber, the apparatus comprising an elongate cover member having a proximal end and a distal end; an elongate support member provided inside the elongate cover member with the elongate cover member and the elongate support member being moveable with respect to each other; and a fistula device supported by the support member, wherein, in use, the elongate cover member is pulled in a proximal direction to allow the fistula device to be released from the delivery apparatus and to deliver the fistula device at a desired location in the wall of the heart.

Preferably, the delivery apparatus comprises a retaining sheath overlying at least a portion of the fistula device, the sheath being moveable to expose the portion of the fistula device covered by the sheath.

Conveniently, the fistula device comprises a stent which is moveable between a collapsed condition when covered by the retaining sheath and an expanded condition when the sheath is removed.

Preferably, the delivery apparatus includes means for urging the fistula device through the wall of the heart.

Conveniently, the elongate support member is substantially straight over its length. The elongate support member conveniently includes a short limb and a long limb defining a generally L-shaped member at the distal end of the elongate support member. The short limb of the generally L-shaped member abuts the fistula device at the distal end of the fistula device.

Ideally, the means for urging the fistula device through the wall of the heart comprises the short limb of the L-shaped member.

Conveniently, the delivery apparatus also includes an inner rod connected to the short limb of the L-shaped member, the inner rod extending into the fistula device for at least a portion of its length.

Advantageously, the fistula device includes a penetrating tip for penetrating through the wall of the heart and facilitating passage of the conduit into and through the heart wall.

Conveniently, the elongate cover member comprises an outer tube which covers the elongate support member and the latter is in the form of an inner tube. The fistula device is moveable between a storage mode in which the fistula device is contained inside the delivery apparatus, with the fistula device lying alongside the elongate cover member at one elongate side of the fistula device and with the elongate support member at the other elongate side of fistula device; and a delivery mode in which the elongate cover member is moved in a proximal direction to release the conduit from the delivery apparatus.

Some of the prior art devices require loading of a delivery device by firstly using a puncture wire to perforate the artery wall and myocardium and then pushing the delivery system containing the fistula device e.g. shunt, stent or conduit over the puncture wire and into position. Other prior art devices have a penetrating tip to facilitate penetration of the heart wall.

However, the delivery apparatus of the present invention has the advantage that the apparatus is loaded by pulling it into position i.e. the conduit is released from the delivery apparatus by pulling the elongate cover member in a proximal direction. Delivery by using this pulling action allows for greater control of the loading procedure since the forces required to puncture the myocardium and artery wall are most easily generated in this way. This loading method also has the advantage of naturally directing the resulting blood flow from the underlying heart chamber distally, and lessens the possibility of a jet of blood impinging directly onto the artery wall. The delivery apparatus of the invention has the further advantage that it is steerable and therefore allows the fistula device to be torqued, thereby facilitating ease of positioning within the coronary artery.

BRIEF DESCRIPTION OF THE DRAWINGS

The present invention will hereinafter be described in conjunction with the following drawings figures, wherein like numerals denote like elements.

DETAILED DESCRIPTION OF THE INVENTION

Figure 1A:
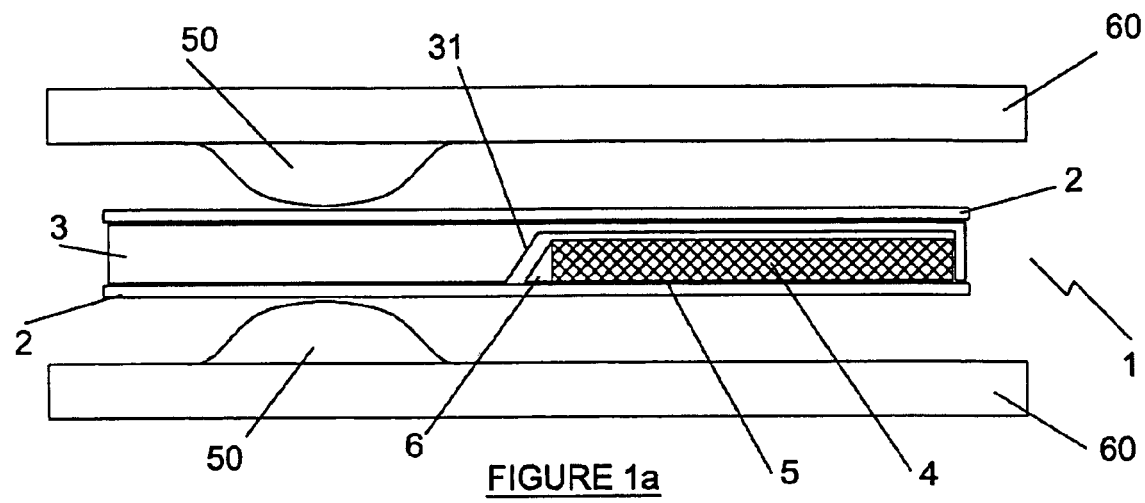
FIG. 1(a) is a schematic drawing of a delivery apparatus in a first embodiment of the invention in position in a target blood vessel, with the elongate cover member of the delivery apparatus fully covering the elongate support member and the sheath-covered fistula device.

The following detailed description of the invention is merely exemplary in nature and is not intended to limit the invention or the application and uses of the invention. Furthermore, there is no intention to be bound by any theory presented in the preceding background of the invention or the following detailed description of the invention.

Referring to FIGS. 1(a) to 1(e) inclusive, a first embodiment of the delivery apparatus for delivering a fistula device 4 to a target vessel is indicated generally by reference number 1. The delivery apparatus 1 comprises an elongate cover member (an outer tube) 2 and an elongate support member (an inner tube) 3, as well as a fistula device 4 and a retaining sheath 5. The fistula device 4 is covered by a retaining sheath 5 which maintains the fistula device in a collapsed condition. In use, when the sheath 5 is removed, the fistula device 4 assumes an expanded condition. The fistula device 4 has a penetrating tip 6 at the proximal end thereof. The elongate support member 3 is of a generally elongate profile with a chamfered edge 31 provided at a point on one elongate side thereof and a generally "L"-shaped member 32 provided towards the distal end of the elongate support member 3. The short limb 33 of the generally "L"-shaped member 32 provides a cover for the distal end of the fistula device 4 and the chamfered edge 31 provides a protective cover for the perforating tip 6 at the proximal end of the fistula device 4. The lesion or obstruction is indicated generally by reference numeral 50 and the coronary artery walls are indicated generally by reference numeral 60 and the myocardium by reference number 70.

The method of delivery of a fistula device using the delivery apparatus 1 will now be described with reference to FIGS. 1(a) to 1(e) inclusive. The delivery apparatus 1 is located in the coronary artery in the position as shown in FIG. 1(a). The elongate cover member is generally in the form of a restraining sheath and this elongate cover member 2 is positioned over the entire length of the elongate support member 3. Thus, the sheath-covered fistula device 4 is enveloped between the elongate support member 3 and the elongate cover member 2.

Figure 1B:
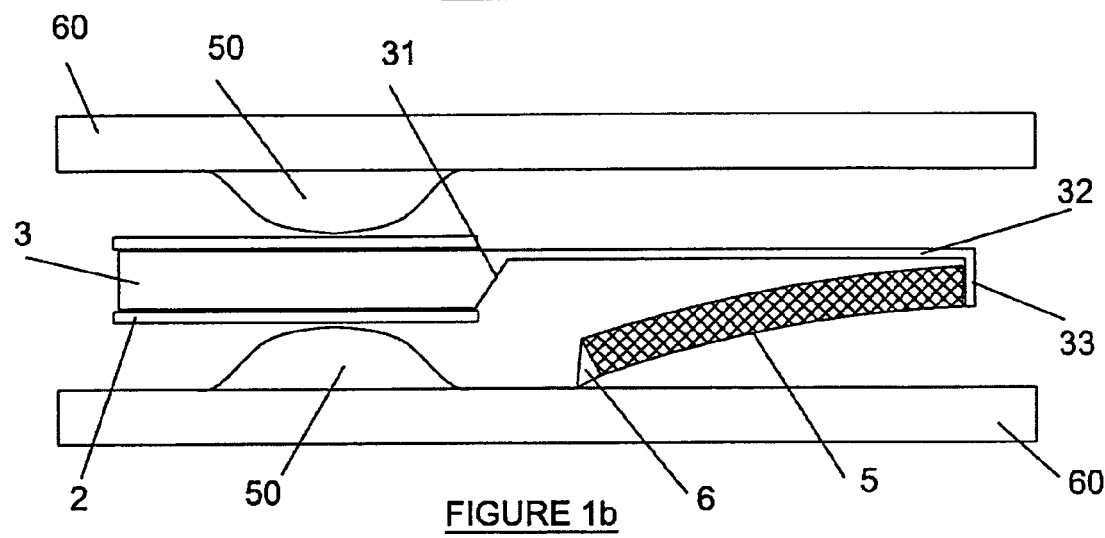
FIG. 1(b) is a schematic diagram showing the delivery apparatus with the elongate cover member withdrawn.

As shown in FIG. 1(b), the elongate cover member 2 is then withdrawn in a proximal direction along the coronary vessel so that the generally L-shaped member 32 of the elongate support member 3 is exposed. The sheath 5 is still covering the fistula device 4 thereby maintaining the fistula device 4 in the collapsed condition. Since the fistula device 4 is not now covered by the elongate cover member 2, the sheath-covered fistula device 4 is released from the delivery apparatus 1 and the fistula device 4 springs outwardly from the elongate support member 3 in an arcuate manner, urging the tip of the fistula device 4 into the wall 60 of the coronary artery.

Figure 1C:
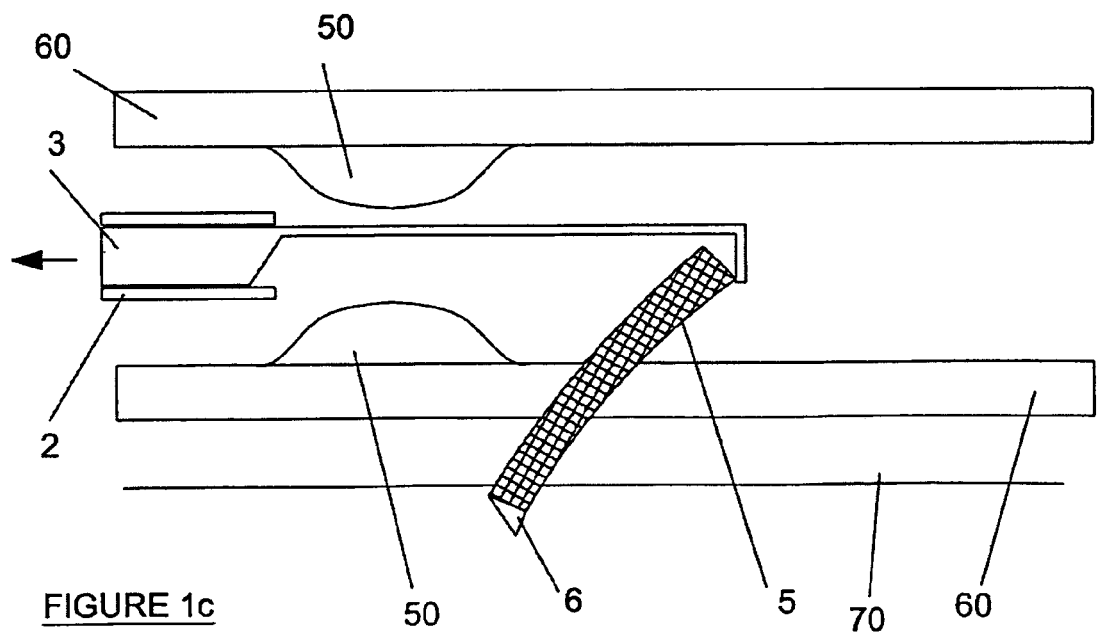
FIG. 1(c) is a schematic diagram showing the fistula device pulled into position through the wall of the target vessel (coronary artery) and into the underlying chamber of the heart.

The entire delivery apparatus 1 is then pulled proximally by the surgeon, so that the short limb 33 of the L-shaped member 32 urges the fistula device 4 through the coronary artery wall and the myocardium 70 and into the underlying heart chamber as shown in FIG. 1(c). The penetration of the fistula device 4 through the coronary artery wall 60 and myocardium 70 is facilitated by the penetrating tip 6 of the fistula device 4 being firstly urged through the coronary artery wall 60 and myocardium 70 thereby creating a channel through which the rest of the fistula device 4 can pass easily. The fistula device 4 is still encased in the retaining delivery sheath 5 so that the fistula device 4 is maintained in the collapsed condition.

Figure 1D:
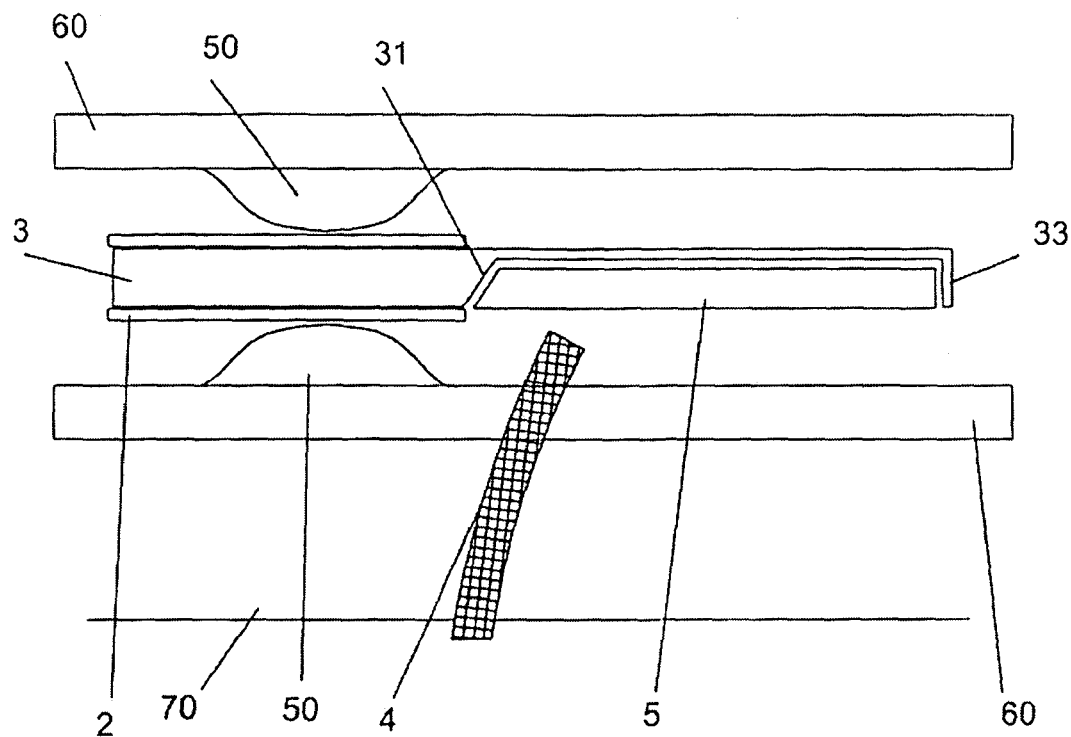
FIG. 1(d) is a schematic diagram showing the tip of the fistula device anchored in the heart wall (myocardium) to allow the retaining sheath to be removed and the retaining sheath is withdrawn from the fistula device.

In the next step, shown in FIG. 1(d) the retaining delivery sheath is removed resulting in the fistula device 4 assuming the expanded condition. To remove the retaining sheath 5, the entire delivery apparatus 1 is pushed distally again, resulting in the retaining sheath 5 being withdrawn from the fistula device 4 and allowing it to "spring open" into the expanded condition.

The penetrating tip 6 of the fistula device 4 is anchored in the myocardium by anchoring means so as to prevent it from being pulled out of the myocardium while the sheath is being removed. One embodiment of such anchoring means is described hereinbelow with reference to FIGS. 4 and 5.

Figure 1E:
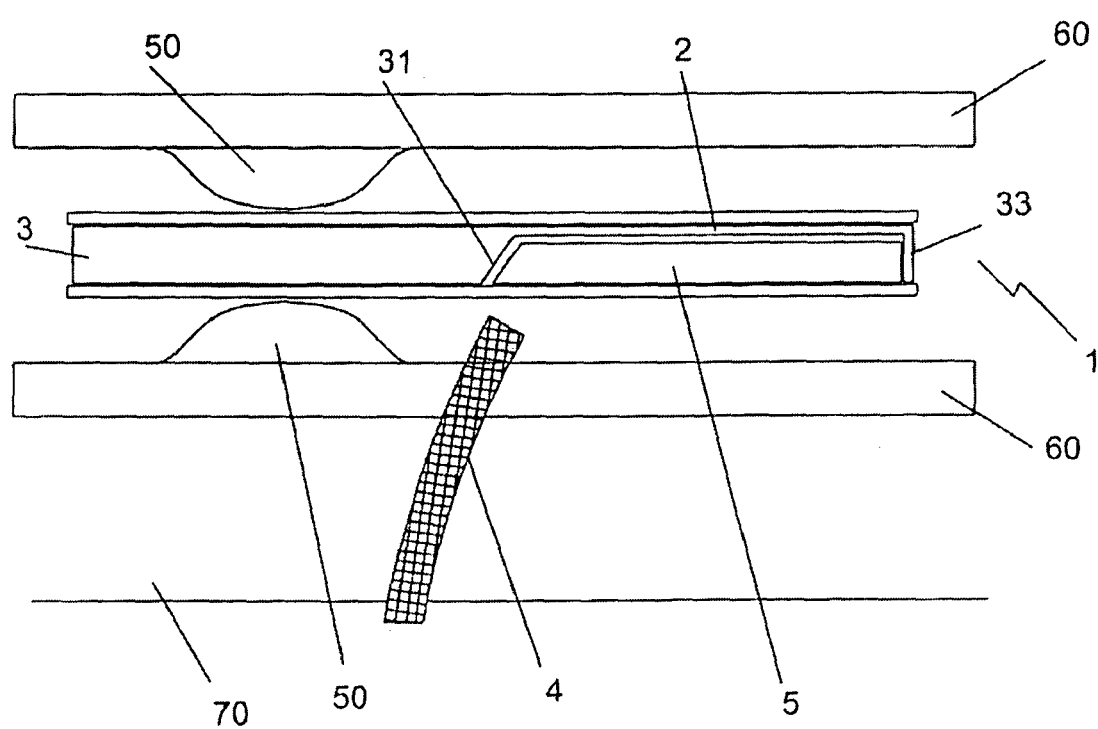
FIG. 1(e) is a schematic diagram showing the elongate cover member tube re-advanced to again cover the elongate support member and the retaining sheath.

Referring to FIG. 1(e), the outer tube is advanced forward to its initial position in which it covers the retaining sheath 5 and the distal end of the elongate support member 3. Finally, the delivery apparatus 1 is then withdrawn from the coronary artery.

In a second embodiment (not shown in the drawings), the delivery apparatus may include a small reservoir for the collection and storage of oxygenated blood during systole (i.e. the period of contraction of the heart during each cardiac cycle) from the underlying chamber and the delivery of this blood to the coronary artery during diastole (i.e. the period of relaxation of the heart during each cardiac cycle). This avoids any problems arising from the provision of blood to the artery during the systolic phase and not during the diastolic phase. This is achieved by ensuring that blood is available at all times of the heart cycle and most importantly during the diastolic phase as naturally happens in the normal coronary vasculature. During the systolic phase, high pressure in the ventricle causes blood to flow into the coronary artery and the blood reservoir. Because of heart muscle contraction, the coronary arteries may have collapsed, thus reducing the available volume for oxygenated blood flow. This is where the reservoir is of use since it stores some excess blood from the ventricle during systole. The wall of its membrane possesses a natural elasticity, since it will most likely be manufactured from a durable elastomer that is capable of repeatedly contracting once the pressure in the ventricle drops (during diastole). This forces the blood out of the reservoir and into the coronary artery making up any shortfall in the supply during this part of the cycle. A non-return valve ensures that no blood returns back into the chamber from where it originally emanated.

The apparatus of the first and second embodiments described above are the preferred forms of the apparatus of the invention.

Figure 2:
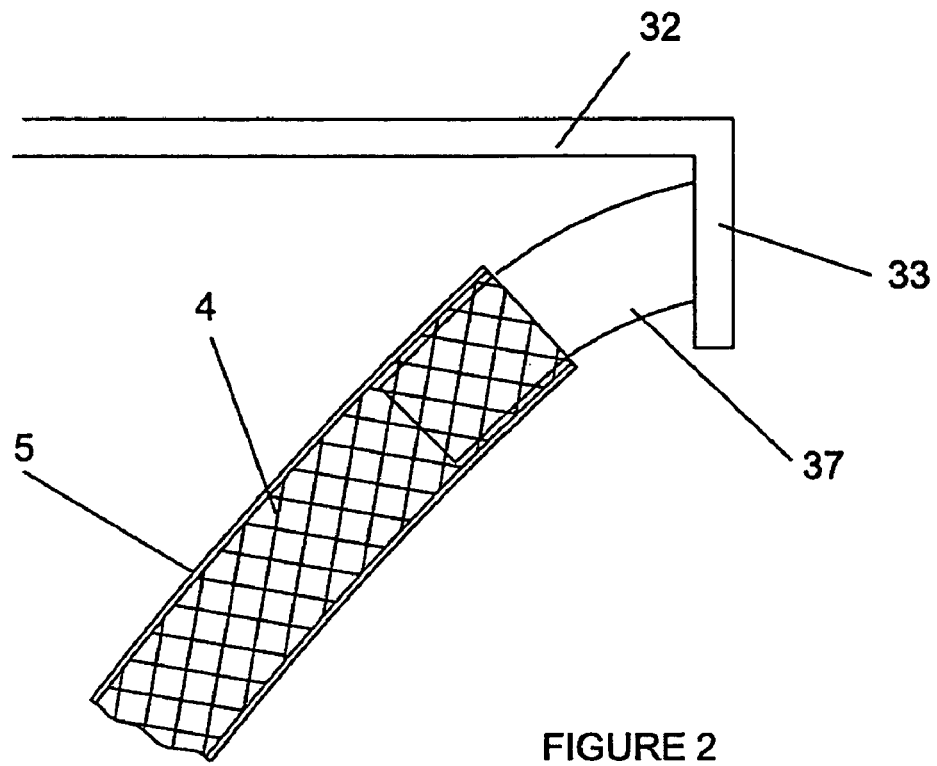
FIG. 2 is a schematic diagram of a means for preventing the fistula device from moving while the sheath is being withdrawn.
Figure 2A:
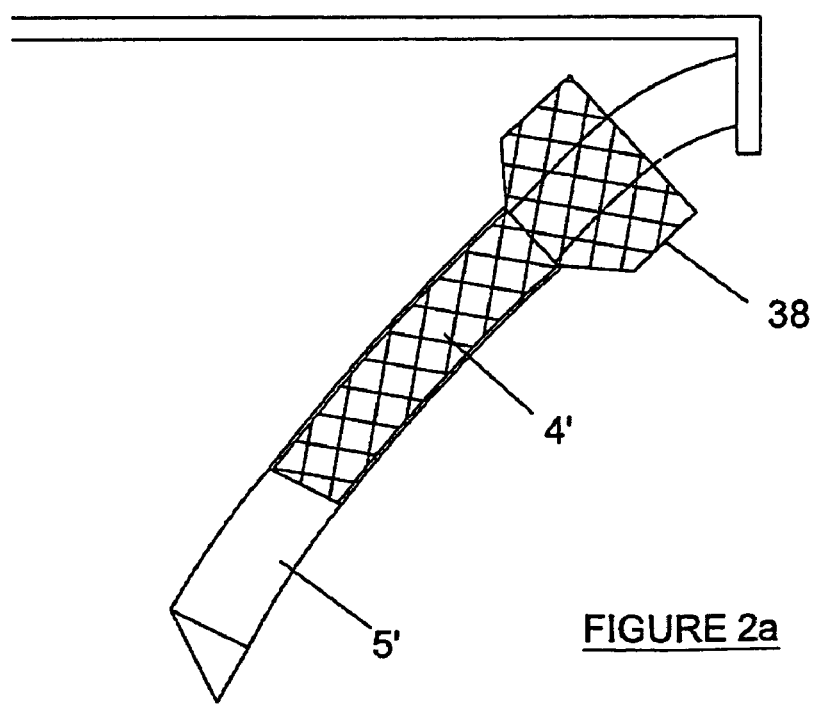
FIG. 2(a) is a schematic diagram of an alternative embodiment of the fistula device of FIG. 2.
Figure 3:
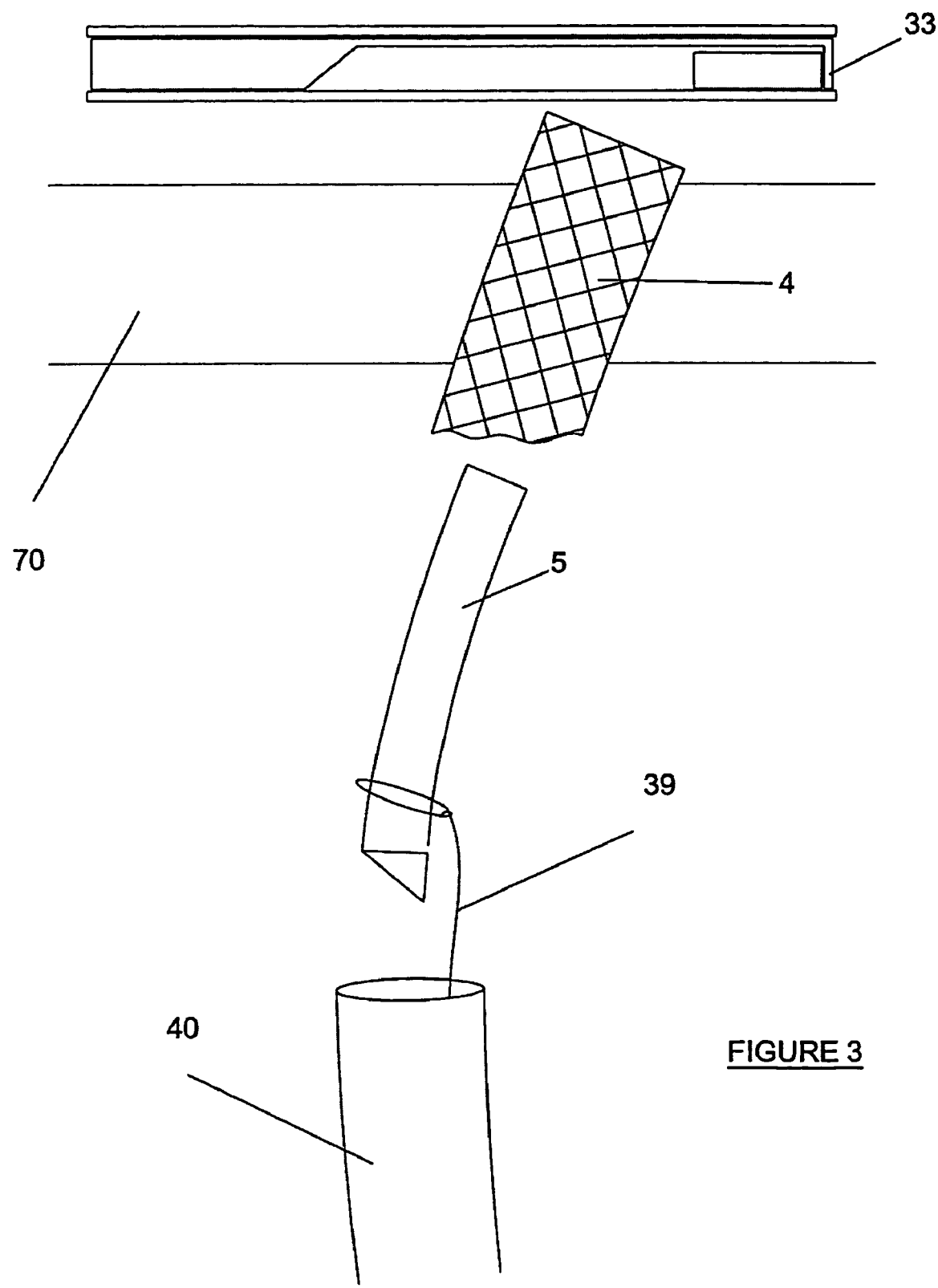
FIG. 3 is a schematic diagram of one embodiment of a means for removing the sheath from the fistula device.

Referring now to FIGS. 2 and 3 of the drawings, a means for preventing movement of the fistula device while the sheath is being removed will now be described. The sheath 5 covers the fistula device 4 and maintains it in a collapsed configuration as described above. The penetrating tip 6 provided at the distal end of the sheath 5 is preferably made from a grade of ferritic steel having magnetic properties. An inner rod 37 is contained within the collapsed fistula device 4 for part of the proximal portion thereof. The fistula device 4 is crimped onto the inner rod 37 at this proximal region. This prevents the fistula device 4 from moving when the sheath 5 is withdrawn. The sheath 5 must now be withdrawn from over the fistula device 4 by pulling it into the chamber of the heart and this necessitates the use of a second device which is loaded inside of the heart chamber. This positioning of the second device within the heart chamber is preferably carried out percutaneously using an extractor catheter 40 which may be passed through the brachial artery in the arm. A wire loop 39 is used to firmly attach to the penetrating tip 6 of the sheath 5 and the magnetic attraction between the penetrating tip 6 and the loop 39 can be used to locate and connect the extractor catheter 40 and the penetrating tip 6 of the sheath 5. As the sheath 5 is withdrawn from the fistula device 4, the fistula device springs open, and the deployed portion of the fistula device then acts as the anchor to prevent the fistula device from being pulled through the myocardium as the sheath is removed. As the fistula device opens, it lifts away from the inner rod 37 thus removing the physical connection between the fistula device 4 and delivery apparatus 1. The loop 39 is used to pull the sheath 5 off the fistula device 4 and pull it inside the extractor catheter 40 allowing it to be easily withdrawn from the patient's body through the chambers of the heart, aorta and finally brachial artery. The elongate cover member 2 is pushed back over the distal portion of the delivery apparatus 1, thereby shielding any jagged edges as the delivery apparatus 1 is being withdrawn through the coronary artery.

As shown in FIG. 2(*a*), in an alternative embodiment the fistula device 4' includes a shoulder portion 38 which further assists in anchoring the fistula device 4' in the myocardium when the sheath 5' is being removed.

Figure 4:
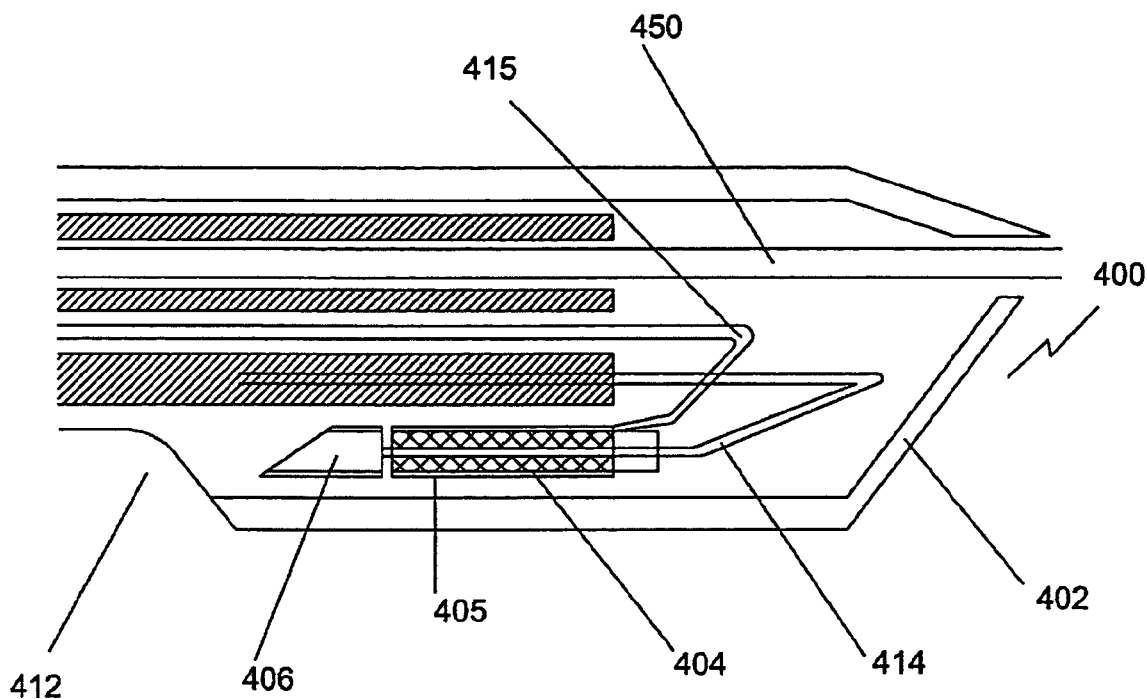
FIGS. 4 and 5 are schematic drawings of an alternative embodiment including a means for anchoring the penetrating tip of the fistula device in the myocardium to prevent it from being pulled therefrom while the sheath is being removed.
Figure 5:
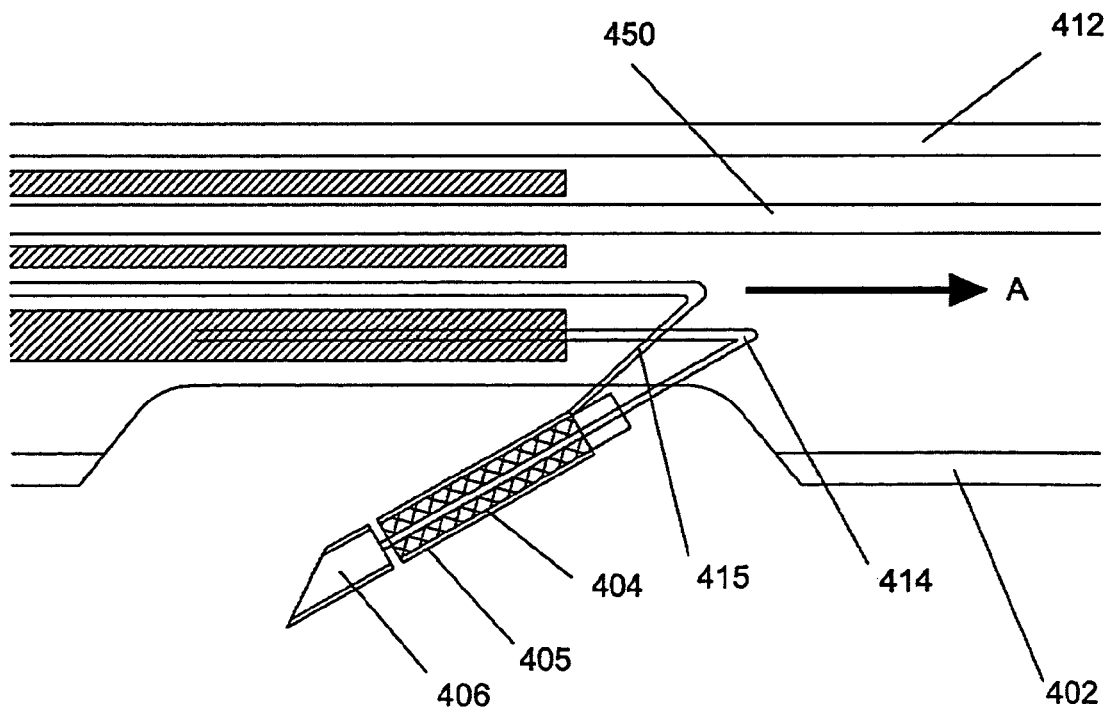

Referring now to FIGS. 4 and 5, an alternative embodiment will be described. The delivery apparatus in this embodiment is indicated generally by reference numeral 400. Like items are indicated with like numerals.

Referring initially to FIG. 4, the delivery apparatus 400 is shown during initial delivery. The apparatus 400 is enveloped within a restraining sheath 402. The apparatus 400 includes a penetrating (cannulating) tip 406 provided on the fistula device 404 and a retaining delivery sheath 405 on the fistula device 404. The apparatus 400 also includes a guide wire 450, a push rod 414 for the ventricular fistula device 404, and a delivery sheath pull wire 415 for the retaining delivery sheath 405. The cover member restraining sheath 402 is provided with a window 412.

Referring now to FIG. 5, the ventricular fistula device 404 in the retaining delivery sheath 405 is deployed to penetrate the myocardium by advancing the restraining sheath 402 distally so that the window 412 aligns with the ventricular fistula device 405. By retracting the complete delivery apparatus, the cannulating tip 406 is urged through the vessel and heart wall. By advancing the delivery sheath pull-wire 415 in the direction of the arrow A as indicated in FIG. 5, the delivery sheath 405 is moved proximally off the ventricular fistula device, the latter being held in position by the ventricular fistula device pushrod 414. After deploying the Ventricular fistula device, the delivery sheath 405 and cannulating tip 406 are recaptured by pulling the restraining sheath 412 proximally once more. The Ventricular fistula device pushrod 414 is shown embedded into the catheter shaft. The catheter shaft is bilumenal construction. Either the pushrod 414 or the pull-wire 415 or both are manufactured of a highly elastic material such as Nitinol.

In an alternative embodiment to that shown in FIGS. 4 and 5, instead of using a self-expanding (Nitinol) Ventricular fistula device, a balloon expandable ventricular fistula device may be employed. One lumen of the bilumenal shaft carries the inflation media/fluid. Once the Ventricular fistula device is expanded, the distal cannulating tip can be retracted through it. Once again the restraining sleeve has a window to release the Ventricular fistula device/sheath, and is moved distally for release and moved proximally for recapture. In both the immediately above referenced embodiments the restraining sheath (402 in FIGS. 4 and 5), could be a short distal sheath anchored to a pulling wire for reduced device profile.

Each of the following 3 alternative methods of deployment of the delivery apparatus are further possible alternative methods of deploying the Ventricular fistula device and address the issue of anchoring the tip of the fistula device in the myocardium so that the fistula device is not pulled out of the heart wall when the sheath is removed.

(1) The Ventricular fistula device is designed such that it is fabricated from Nitinol and requires no sheath; this is achieved by a customised elevated transformation temperature so that it remains martensitic beyond body temperature of 37° C., the transformation to superelastic austenitic Nitinol would be prompted by means of radio frequency (RF) or electrical resistance heating;

(2) A bio-resorbable sheath is employed so that it gradually releases a self-expanding structure over a suitable period of time;

(3) A bio-resorbable sheath is employed in unison with a rip-chord type device so that the self-expanding structure is immediately released to create the fistula and the sheath is then resorbed over a suitable period of time.

Figure 6:
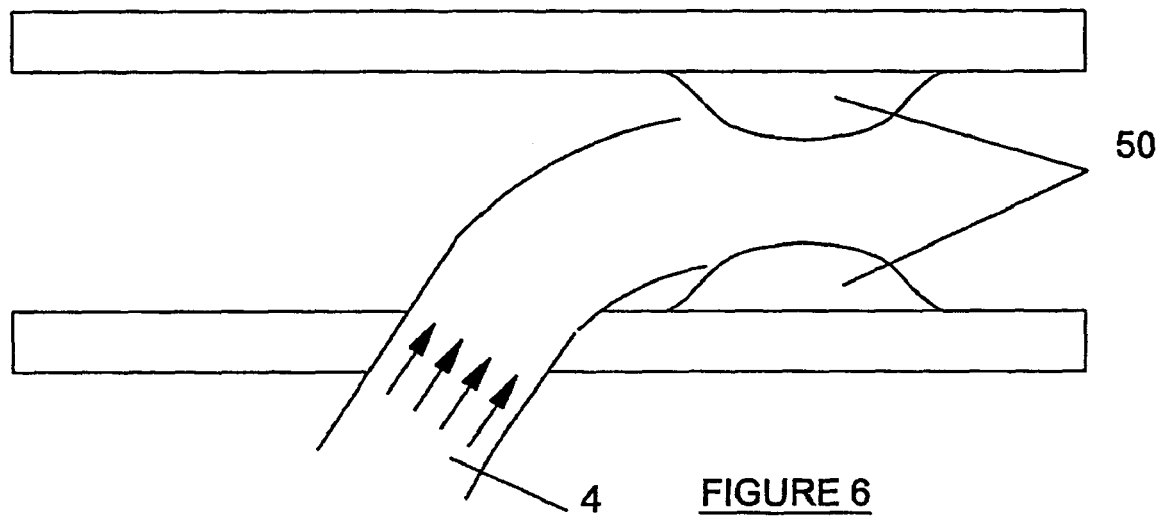
FIG. 6 is a schematic diagram of an alternative embodiment of the apparatus of the invention in which, in use, the fistula device is positioned proximal to the lesion.
Figure 6A:
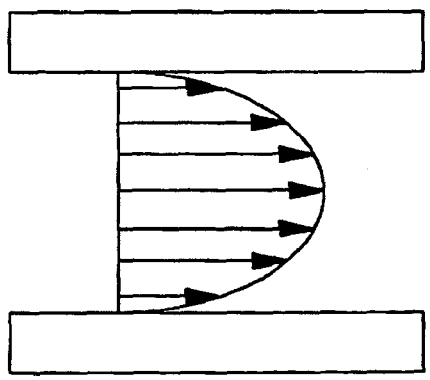
FIG. 6(a) is a schematic diagram showing the normal blood flow velocity profile without a fistula device.
Figure 6B:
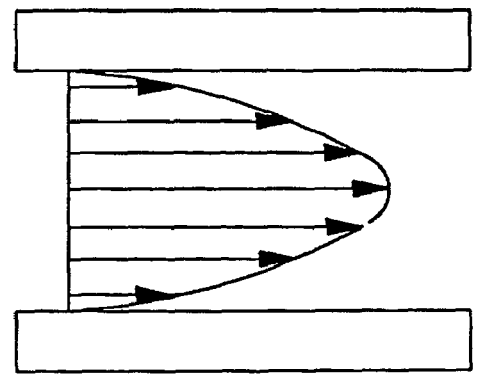
FIG. 6(b) is a schematic diagram showing the altered blood flow velocity profile arising from use of a fistula device proximal to lesion.

In some instances, a lesion must actually be crossed to deliver the device to the intended site. Depending upon the severity of the lesion, this will present varying degrees of difficulty. In order to avoid this, an alternative embodiment of the delivery apparatus, shown in FIGS. 6 and 6*b*, provides a device that is positioned proximal to the lesion, thereby avoiding any problems arising from crossing the lesion. The normal velocity profile of the steady-state blood flow in the coronary artery is shown in FIG. 6(*a*). This velocity profile is changed by directing a 'jet' of high pressure blood down the centre of the artery. In largely concentric lesions, this serves to increase the total volumetric flow of blood to the distal portion of the artery, consequently supplying a greater amount of oxygen to the affected muscle region. A potential drawback of this design is the potential effect of the blood flow on the lesion. The altered sheer stress on the wall of the artery will undoubtedly lead to growth of the lesion over time. Of course the rate at which the lesion grows, and the age of the patient may determine whether using the apparatus in this embodiment is an appropriate method of treatment.

The change in the normal velocity profile is expressed mathematically as Volumetric flow rate $Q=\int VdA$. Placing the fistula device proximal to the lesion attempts to change the distribution of V with respect to radial distance from centre of artery and thereby get a high flow rate down the artery.

Figure 7:
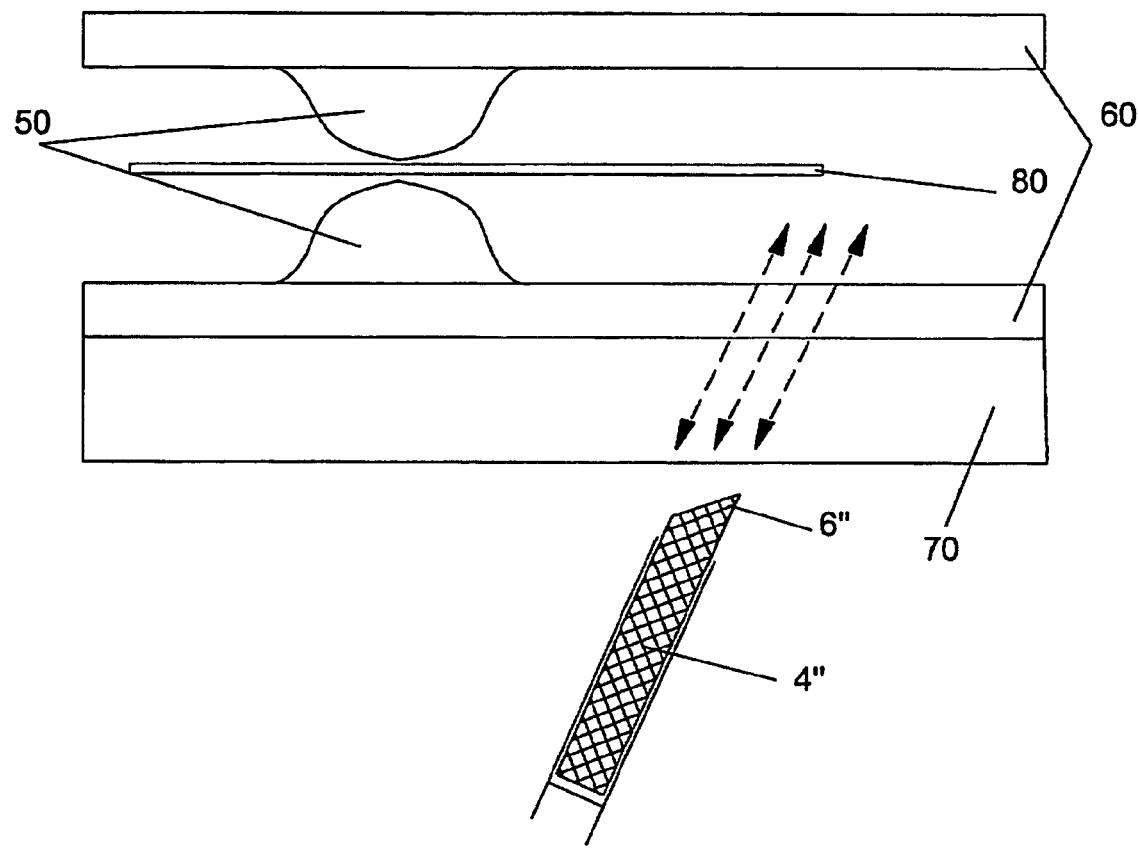
FIG. 7 is a schematic diagram of a further alternative embodiment of the apparatus in which the fistula device is guided out to a coronary artery from inside a chamber of the heart.

In an alternative embodiment shown in FIG. 7, the delivery apparatus 1 may be loaded from inside the Heart Chamber out to the Coronary Artery. The embodiment of the apparatus is an attempt to avoid the issue of crossing the lesion 50. A guidewire 80 is advanced past the lesion 50 and magnetic means are employed to communicate between the tip of this guidewire 80 and the tip 6" of the fistula device 4" inside the heart chamber. The magnetic attraction between the tip of the guidewire 80 and the tip 6" helps guide the fistula device 4" through the heart wall and safely into the coronary artery distal of the lesion 50.

Figure 8:
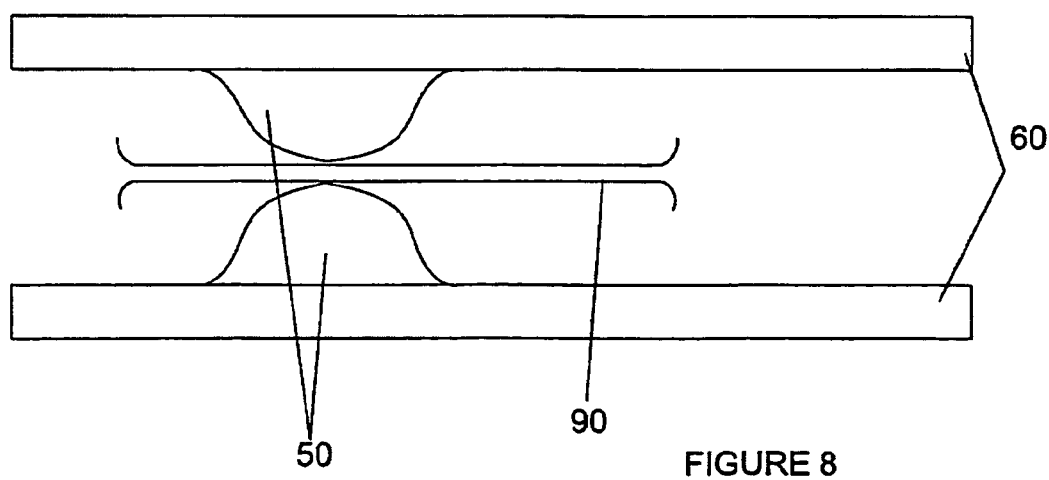
FIG. 8 is a schematic diagram of another alternative embodiment in which a tunnel-like device is included in the delivery apparatus of the present invention.

As shown in FIG. 8, in a further alternative embodiment, the delivery apparatus may include a tunnel device 90 to aid the flow of blood across the lesion 50 in order to open it slightly. In this sense, the device is essentially functioning as a solid stent. The tunnel device 90 may also be used to aid the passage of the delivery apparatus 1 across the lesion 50.

What is claimed is:

1. An apparatus for delivering a fistula device into a wall of a patient's heart to place the fistula device in fluid communication with a heart chamber, the apparatus comprising:
   an elongate cover member having a proximal end and a distal end;
   an elongate support member slidably disposed within the cover member and comprising, at a distal end, a first elongate limb and a second limb shorter than the first elongate limb, the first and second limbs forming an L-shaped member;
   a fistula device being supported by the elongate support member, the second limb of the elongate support member being disposed distal to the fistula device and being configured to push the fistula device proximally upon proximal movement of the elongate support member; and
   a removable retaining sheath overlying at least a portion of the fistula device wherein the fistula device is transformable from a collapsed state to an expanded state when the retaining sheath is removed;
   wherein the fistula device or the retaining sheath comprises a penetrating tip at a proximal end of the fistula device or retaining sheath, the penetrating tip being configured to penetrate the wall of the heart upon proximal movement of the elongate support member to facilitate passage of the fistula device therethrough; and
   wherein, in use, the elongate cover member is moveable along the support member so as to release the fistula device from the delivery apparatus to permit delivery of the fistula device to a desired location in the wall of the heart.

2. An apparatus according to claim 1 further comprising a rod coupled to the second limb for extending at least partially into the fistula device.

3. An apparatus according to claim 1 wherein the elongate cover member is tubular.

4. An apparatus according to claim 1 wherein the elongate support member is tubular.

5. An apparatus according to claim 1 wherein the elongate support member includes a chamfered edge to protect the penetrating tip.

6. An apparatus according to claim 5 wherein the fistula device comprises anchoring means to prevent the fistula device from being displaced when the retaining sheath is removed.

7. An apparatus according to claim 1 wherein the fistula device is self-expanding.

8. An apparatus according to claim 1 wherein the fistula device is balloon expandable.

9. An apparatus according to claim 1 wherein the fistula device is heat-expanded.

10. An apparatus according to claim 1 wherein the retaining sheath is bio-resorbable.

* * * * *